United States Patent [19]

Grollier

[11] Patent Number: 5,275,626
[45] Date of Patent: Jan. 4, 1994

[54] METHOD FOR DYEING KERATINOUS FIBRES USING A MONOHYDROXYINDOLE OR DIHYDROXYINDOLE AND A NON-OXIDISTING AROMATIC CARBONYL DERIVATIVE AND DYEING AGENT

[75] Inventor: Jean F. Grollier, Paris, France
[73] Assignee: L'Oreal, Paris, France
[21] Appl. No.: 831,064
[22] Filed: Feb. 4, 1992

[30] Foreign Application Priority Data

Feb. 4, 1991 [FR] France ................... 91 01234

[51] Int. Cl.$^5$ .................................. A61K 7/13
[52] U.S. Cl. .............................. 8/405; 8/406; 8/407; 8/409; 8/423; 424/70
[58] Field of Search ............. 8/405, 406, 407, 409, 8/423, 634; 424/70

[56] References Cited

U.S. PATENT DOCUMENTS

| | | | |
|---|---|---|---|
| 5,034,015 | 7/1991 | Junino et al. | 8/405 |
| 5,053,053 | 10/1991 | De Labbey et al. | 8/408 |
| 5,064,442 | 11/1991 | Grollier | 8/405 |

FOREIGN PATENT DOCUMENTS

| | | |
|---|---|---|
| 0271186 | 6/1988 | European Pat. Off. |
| 0376776 | 7/1990 | European Pat. Off. |
| 2626173 | 7/1989 | France |
| 2093867 | 9/1982 | United Kingdom |
| 2119411 | 11/1983 | United Kingdom |

OTHER PUBLICATIONS

French Search Report of FR 91 01234 (1991, no month available).

*Primary Examiner*—Paul Lieberman
*Assistant Examiner*—William S. Parks
*Attorney, Agent, or Firm*—Cushman, Darby & Cushman

[57] ABSTRACT

The present invention relates to a method for dyeing keratinous fibers, characterized in that the following are applied to the fibers:
a) a composition (A) containing, in a medium appropriate for dyeing, at least one monohydroxyindole or dihydroxyindole, this application being preceded or followed by the application of
b) a composition (B) containing, in a medium appropriate for dyeing, at least one aromatic carbonyl derivative chosen from hydroxyacetophenones, hydroxybenzophenones, 2-hydroxy-1,4-benzoquinones, hydroxy-1,4-naphthoquinones, amino-1,4-naphthoquinones, hydroxy-9,10-anthraquinones and amino-9,10-anthraquinones.

It also relates to the dyeing agents for carrying it out.

19 Claims, No Drawings

METHOD FOR DYEING KERATINOUS FIBRES USING A MONOHYDROXYINDOLE OR DIHYDROXYINDOLE AND A NON-OXIDISTING AROMATIC CARBONYL DERIVATIVE AND DYEING AGENT

The present invention relates to a new method for colouring keratinous fibers, and more particularly human keratinous fibers, such as the hair, using at least one monohydroxyindole or dihydroxyindole and at least one non-oxidizing aromatic carbonyl derivative.

There has in the past already been proposed dyeing of keratinous fibers, and in particular the hair, with the aid of hydroxyl derivatives of indole. In fact, it is known that the natural synthesis of eumelanins from tyrosine proceeds in several steps, one of which consists in the formation of 5,6-dihydroxyindole, which oxidizes to form a pigment which is one of the main constituents of eumelanin.

Thus, French Patents Nos. 1,166,172 and 1,264,707, in particular, propose coloring the hair using aqueous compositions containing 5,6-dihydroxyindole. Using compositions of this type it is possible to dye the hair in light shades by an application of the product or in increasingly lasting shades by superimposition of the application.

However, these methods do not make it possible to obtain a sufficiently wide range of varied shades, in particular the shades known as "with glints", which are particularly desired in hair coloring.

Methods for hair dyeing using indole derivatives, in which methods the color is developed by means of oxidizing systems, have also been described. Oxidizing systems of this type are described, in particular, in European. Patent Application No. 376,776 and other known oxidizing agents comprise hydrogen peroxide, on its own or in combination with an iodide, periodates, bromates, persulphates, perborates and nitrites, in particular.

The applicant has now demonstrated that it was possible to obtain, in a method which does not require oxidizing development other than that by atmospheric oxygen, varied shades which are very natural or rich in glints, without having the disadvantages of the prior art. In fact, in hair dyeing it is generally difficult to obtain natural shades and a uniformity of color on hair which is long and/or sensitized by permanent waving, dyeing or bleaching, and over its entire length.

The method according to the invention is a method for dyeing keratinous fibers, in particular the hair, using, in a two-stage process, the application of at least one indole derivative, this application being preceded or followed by the application of at least one non-oxidizing aromatic carbonyl derivative.

This method makes it possible to obtain a good covering of white hair in a uniform natural shade over the entire head of hair without altering the mechanical properties of the hair. These dyeings are of low selectivity and also have a good resistance to perspiration, to washing, to light and to chemical and atmospheric attack.

The method for dyeing keratinous fibers is characterized in that the following are applied to the fibers:

a) a composition (A) containing, in a medium appropriate for dyeing, at least one monohydroxyindole or dihydroxyindole, this application being preceded or followed by the application of b) a composition (B) containing, in a medium appropriate for dyeing, at least one aromatic carbonyl derivative chosen from hydroxyacetophenones, hydroxybenzophenones, 2-hydroxy-1,4-benzoquinones, hydroxy-1,4-naphthoquinones, amino-1,4-naphthoquinones, hydroxy-9,10-anthraquinones and amino-9,10-anthraquinones.

Another subject of the invention comprises a multicomponent dyeing agent, preferably in the form of a "dyeing kit" or "dyeing set" for carrying out the method according to the invention.

The following are used as monohydroxyindole or dihydroxyindole, according to the invention: the compounds of formula (I):

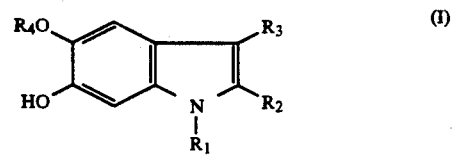

in which:

$R_1$, $R_3$ and $R_4$, which may be identical or different, represent a hydrogen atom or a $C_1$–$C_4$ alkyl group;

$R_2$ denotes a hydrogen atom, a $C_1$–$C_4$ alkyl group or a carboxyl group; and the corresponding alkali metal, alkaline earth metal, ammonium and amine salts of these compounds.

The redox potential of the indole derivatives of formula (I), measured at pH 7 on a vitreous carbon electrode by voltammetry, is, according to the invention, less than 200 mV.

Amongst these indoles, the preferred compounds according to the invention are chosen from:
5,6-dihydroxyindole,
2-methyl-5,6-dihydroxyindole,
3-methyl-5,6-dihydroxyindole,
1-methyl-5,6-dihydroxyindole,
2,3-dimethyl-5,6-dihydroxyindole,
5-methoxy-6-hydroxyindole and
2-carboxy-5,6-dihydroxyindole.

The non-oxidizing aromatic carbonyl derivatives are in particular chosen from the following compounds:
hydroxyacetophenones or hydroxybenzophenones which are chosen from the compounds of formula (II):

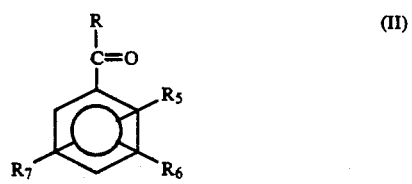

in which:

$R_5$, $R_6$ and $R_7$, which may be identical or different, denote a hydrogen atom or a hydroxyl or methoxy group, at least one of $R_5$, $R_6$ and $R_7$ denoting hydroxyl, and R represents a methyl group or $R_8$, $R_8$ representing a

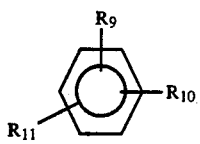

radical, where $R_9$, $R_{10}$ and $R_{11}$, which may be identical or different, represent a hydrogen atom or a hydroxyl or methoxy group;

2-hydroxy-1,4-benzoquinones which are chosen form the compounds of formula (III):

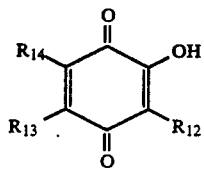

in which:

$R_{12}$, $R_{13}$ and $R_{14}$, which may be identical or different, represent a hydrogen atom or a $C_1$-$C_4$ alkoxy, hydroxyl, $C_1$-$C_4$ alkyl, amino, $C_1$-$C_4$ aminoalkyl or parahydroxyphenyl group;

hydroxy-1,4-naphthoquinones or amino-1,4-naphthoquinones which are chosen from the compounds of formula (IV):

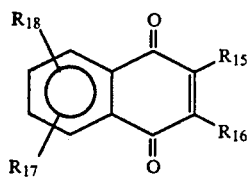

in which:

$R_{15}$ and $R_{16}$, which may be identical or different, represent a hydrogen or chlorine atom or a hydroxyl, methoxy, methyl, isopentenyl, acetyl or —$SCH_2COOH$ group, or a —$NR_{19}R_{20}$ group, where $R_{19}$ and $R_{20}$, which may be identical or different, represent a hydrogen atom or a methyl or hydroxyethyl group, and $R_{17}$ and $R_{18}$, which may be identical or different, represent a hydrogen atom or a hydroxyl, methoxy or methyl group, at least one of $R_{15}$, $R_{16}$, $R_{17}$ and $R_{18}$ representing hydroxyl or at least one of $R_{15}$ and $R_{16}$ representing —$NR_{19}R_{20}$;

hydroxy-9,10-anthraquinones or amino-9,10-anthraquinones which are chosen from the compounds of formula (V):

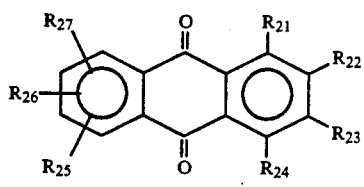

in which:

$R_{21}$ to $R_{27}$, which may be identical or different, represent a hydrogen or chlorine atom or a hydroxyl, methyl, $SO_3M$, $COOM$ or $NR_{28}R_{29}$ group, where M denotes a hydrogen, Na or K atom, and $R_{28}$ and $R_{29}$, which may be identical or different, represent a hydrogen atom or a $C_1$-$C_4$ alkyl or $C_1$-$C_4$ monohydroxyalkyl group, at least one of $R_{21}$ to $R_{27}$ representing a hydroxyl or $NR_{28}R_{29}$ group.

Amongst these non-oxidizing carbonyl derivatives, according to the invention, the following compounds may be mentioned:

2-hydroxyacetophenone,
2,5-dihydroxyacetophenone,
2,6-dihydroxyacetophenone,
4-hydroxy-3-methoxyacetophenone,
3,4,5-trihydroxyacetophenone,
2',2'-dihydroxybenzophenone,
2-hydroxybenzophenone,
2,2',4,4'-tetrahydroxybenzophenone and
3,4,2',4',6'-pentahydroxybenzophenone;
2,5-dihydroxy-1,4-benzoquinone,
2,5-dihydroxy-3-ethyl-1,4-benzoquinone,
2,5-dihydroxy-3,6-dimethoxy-1,4-benzoquinone,
2,5-dihydroxy-3-methyl-6-isopropyl-1,4-benzoquinone,
2,5-dihydroxy-3,6-bis-p-hydroxyphenyl-1,4-benzoquinone,
2-hydroxy-3-methyl-6-methoxy-1,4-benzoquinone,
2-hydroxy-3-methyl-5,6-dimethoxy-1,4-benzoquinone,
2-hydroxy-3-methoxy-6-methyl-1,4-benzoquinone and
2,3,5,6-tetrahydroxy-1,4-benzoquinone;
2-hydroxy-3-isopentenyl-1,4-naphthoquinone,
2-hydroxy-3-amino-7-methoxy-1,4-naphthoquinone,
2-hydroxy-3-N-methylamino-1,4-naphthoquinone,
2-hydroxy-6-methoxy-1,4-naphthoquinone,
2-hydroxy-5-methoxy-1,4-naphthoquinone,
2-hydroxy-8-methoxy-1,4-naphthoquinone,
2-hydroxy-5,8-dimethoxy-1,4-naphthoquinone,
2-hydroxy-3-acetyl-1,4-naphthoquinone,
5-hydroxy-2-methoxy-1,4-naphthoquinone,
5-hydroxy-3-dimethylamino-1,4-naphthoquinone,
5-hydroxy-3-methoxy-1,4-naphthoquinone,
5-hydroxy-2-methyl-1,4-naphthoquinone,
5-hydroxy-2-methyl-3-chloro-1,4-naphthoquinone,
5-hydroxy-2-carboxymethylthio-1,4-naphthoquinone,
5-hydroxy-3-carboxymethylthio-1,4-naphthoquinone,
5,8-dihydroxy-1,4-naphthoquinone,
5,8-dihydroxy-2-chloro-1,4-naphthoquinone,
2,7-dihydroxy-1,4-naphthoquinone,
5,7-dihydroxy-1,4-naphthoquinone,
3,5-dihydroxy-2-methyl-1,4-naphthoquinone,
3,5-dihydroxy-1,4-naphthoquinone,
2,6-dihydroxy-1,4-naphthoquinone,
2,3-dihydroxy-5-methoxy-1,4-naphthoquinone,
2,3-dihydroxy-7-methoxy-1,4-naphthoquinone,
3,6,8-trihydroxy-1,4-naphthoquinone,
2,3,5-trihydroxy-1,4-naphthoquinone,
2,6,7-trihydroxy-1,4-naphthoquinone,
2,3,5,8-tetrahydroxy-1,4-naphthoquinone and
1,4-dihydroxy-9,10-anthraquinone,
1,5-dihydroxy-9,10-anthraquinone,
1,8-dihydroxy-9,10-anthraquinone,
2,6-dihydroxy-9,10-anthraquinone,
1,2,5,8-tetrahydroxy-9,10-anthraquinone,
1,2,3,5,6,7-hexahydroxy-9,10-anthraquinone,
1,8-dihydroxy-3-methyl-9,10-anthraquinone,
1,3,8-trihydroxy-6-methyl-9,10-anthraquinone,
5,8-dichloro-1,4-dihydroxy-9,10-anthraquinone, the sodium salt of 1,2-dihydroxy-9,10-anthraquinone-3-sulphonic acid, the sodium salt of 1,2,4-trihydroxy-9,10-anthraquinone-3-sulphonic acid,
1-hydroxyanthraquinone, 2-hydroxyanthraquinone,
1,8-dihydroxy-3-carboxy-9,10-anthraquinone,
1,4,5,8-tetraaminoanthraquinone and
1,4-diaminoanthraquinone.

Amongst these compounds, the following are particularly preferred:
5,8-dihydroxy-1,4-naphthoquinone,
1,2,5,8-tetrahydroxyanthraquinone and
1,4,5,8-tetraaminoanthraquinone.

Amongst the non-oxidizing carbonyl compounds, the following compounds may also be mentioned:
2,5-dihydroxy-3-methyl-1,4-benzoquinone,
2,5-dihydroxy-3-methoxy-6-methyl-1,4-benzoquinone,
2-hydroxy-1,4-naphthoquinone,
2-hydroxy-3-methyl-1,4-naphthoquinone,
2,5-dihydroxy-1,4-naphthoquinone,
2,3-dihydroxy-1,4-naphthoquinone,
2,5,7-trihydroxy-1,4-naphthoquinone,
5-hydroxy-1,4-naphthoquinone,
2,5,8-trihydroxy-1,4-naphthoquinone,
2-hydroxy-3-methoxy-1,4-naphthoquinone,
2-carboxy-1-methyl-3,5,6,8-tetrahydroxy-anthraquinone,
1,2-dihydroxyanthraquinone,
1,2,4-trihydroxyanthraquinone and
3-carboxy-1,2,4-trioxyanthraquinone.

The compounds according to the invention are known and may be obtained by synthesis or, if appropriate, from organisms producing them or plants containing them when they are of natural origin. In the latter case, the products containing these dyes may be used either in the form of extracts or in the form of a homogenized products of all or part of the organisms or plants.

The compositions (A) and (B), and in particular the composition (B), which can be used in the method of the invention may also contain other direct natural dyes customarily used for dyeing keratinous fibers. Thus, it is also possible to use isatin, purpurogallin, pyocyanine, curcumin, indigo, hematoxyline, brasilin, riboflavin, bixin, β-carotene, rutin and quercetin. It is also possible to use dyes nitrated on the benzene ring.

According to the invention, the proportion of monohydroxyindole or dihydroxyindole of formula (I) present in the composition (A) is between 0.05 and 5% by weight of this composition and preferably between 0.05 and 3% by weight with respect to the total weight of this composition (A).

The proportion of non-oxidizing aromatic carbonyl derivative contained in the composition (B) is, according to the invention, between 0.01 and 5% by weight and preferably between 0.05 and 3% by weight with respect to the total weight of the composition (B).

According to the invention, the aqueous or anhydrous compositions (A) and (B) are used in the form of liquids of higher or lower viscosity, or in the form of creams, aqueous or anhydrous gels, oils or powders to be diluted with a liquid at the time of use and also termed "cataplasm".

In a first embodiment of the invention, the medium appropriate for dyeing which is used for the two compositions (A) and (B) is aqueous. Its pH may vary between 2 and 10 and it is preferably between 3 and 9.5, it being possible to adjust this value to the desired value with the aid of known alkalinizing agents or acidifying agents.

These compositions may contain anionic, cationic, nonionic or amphoteric surfactants or mixtures of such surfactants. Surfactants which may be mentioned more particularly are soaps, alkylbenzenesulphonates, alkylnaphthalenesulphonates, sulphates or ether-sulphates or -sulphonates of fatty alcohols, quaternary ammonium salts, diethanolamides of fatty acids, polyoxyethylenated or polyglycerolated acids or alcohols or amides, polyoxyethylenated or polyglycerolated alkylphenols and alkylpolyglycosides.

According to the invention, the surfactants are present in the compositions which can be used for carrying out the method in proportions of between 0.1 and 55% by weight of the compositions, and preferably between 1 and 40% by weight with respect to the total weight of each of these compositions.

The aqueous medium appropriate for dyeing may also contain organic solvents such as, for example, lower alkanols, such as ethanol or isopropanol, polyols, such as glycerol, glycols or glycol ethers, such as ethylene glycol, propylene glycol, ethylene glycol monobutyl ether, diethylene glycol monoethyl ether and diethylene glycol monomethyl ether, as well as analogous products or mixtures thereof.

Preferably, these solvents are then present in proportions ranging from 1 to 60% by weight with respect to the total weight of the composition, and more particularly of between 3 and 30% by weight.

The compositions for carrying out the method according to the invention may also contain anionic, nonionic, cationic or amphoteric polymers or mixtures thereof, in proportions of between 0.1 and 5% by weight with respect to the total weight of the composition.

In this first embodiment of the invention, the compositions may be thickened using thickeners. Amongst the possible thickeners, the following may be mentioned for example: sodium alginate, gum Arabic, guar gum or carob gum, xanthan gum, pectins, cellulose derivatives, such as methylcellulose, hydroxyethylcellulose, hydroxymethylcellulose, hydroxypropylcellulose and carboxymethylcellulose, and diverse polymers having a thickening action, such as acrylic acid derivatives. It is also possible to use inorganic thickeners, such as bentonite.

When the compositions contain thickeners, the latter are present in proportions of between 0.1 and 5% by weight with respect to the total weight of the composition, and in particular in proportions of between 0.5 and 3% by weight.

In addition, these compositions may contain other adjuvants customarily used in compositions for dyeing keratinous fibers, in particular for dyeing hair, such as penetrating agents, sequestering agents, antioxidants, buffers, perfumes and the like.

A preferred form of the invention consists in using, for composition (B), an anhydrous medium such as is described in French Patent Application No. 2,526,031. An anhydrous medium is understood to be a medium which does not contain more than 1% of water.

According to this variant, the anhydrous medium consists of a mixture of at least one anhydrous solvent and at least one or more anhydrous surfactants, the composition containing at least 15% of solvent and at least 20% of surfactant.

According to the invention, it is possible to use cosmetically acceptable solvents chosen from saturated $C_2$–$C_{20}$ monoalcohols, such as ethanol, isopropanol, cetyl alcohol or octyldodecanol; polyols, such as alkylene glycols, such as ethylene glycol, propylene glycol, glycerol or diethylene glycol; glycol ethers, such as mono-, di- and tri-ethylene glycol monoalkyl ethers, such as, for example, ethylene glycol monoethyl ether, ethylene glycol monobutyl ether or diethylene glycol monoethyl ether; esters, such as, for example, ethylene glycol monomethyl ether acetate or ethylene glycol monoethyl ether acetate; esters of fatty acids and saturated lower alcohols, such as isopropyl myristate or isopropyl palmitate, and mixtures thereof.

Amongst these solvents, the solvents particularly preferred are chosen from ethanol, cetyl alcohol, propylene glycol, ethylene glycol monoethyl ether or ethylene glycol monobutyl ether.

According to this variant, the surfactants are chosen from anhydrous surfactants of anionic, nonionic, cationic or amphoteric type, or mixtures thereof. The following may be mentioned more particularly: polyoxyethylenated fatty alcohols, polyoxyethylenated alkylphenols or naphthols, monoalkyltrimethylammonium halides, dialkyldimethylammonium halides, soaps and polyglycerolated fatty alcohols. The particularly preferred surfactants are the nonionic surfactants.

In addition, these anhydrous compositions may contain an anhydrous alkaline or acidifying agent, such as, for example, citric acid, ascorbic acid, acetic acid, lactic acid and alkanolamines, such as, preferably, those which are totally substituted by an amino group, such as dimethylaminoethanol.

The anhydrous compositions may also contain other anhydrous additives, such as are used in cosmetics. Amongst these additives, the following may be mentioned: perfumes, thickeners, hair treatment agents, antioxidants, vegetable or mineral oils, preservatives and organic salts.

These compositions according to the invention may be applied as such to the wet hair or, according to a second mode of application, they may be diluted just before use. In the latter case, at the time of dyeing, the compositions are diluted with an aqueous solution such that the ratio by weight between the anhydrous composition according to the invention and the aqueous solution is between 0.25 and 2.

The aqueous solution used for the dilution may consist of pure water but also of any other complex aqueous liquid of higher or lower viscosity, such as a carrier customarily used in tinctorial compositions for hair.

In this case, the components of the cosmetic composition may be any type of cosmetically acceptable ingredients, which may or may not be anhydrous, such as are customarily used in this type of composition and described in general above.

In another particularly preferred embodiment of the composition (B), according to the invention, this composition is applied in the form of a cataplasm, that is to say in the form of powders to be diluted with a liquid at the time of use.

In this embodiment the dyes are prepared in the form of a powder which is stable on storage and introduced into a solid medium which may consist of powders, flours or starchy or mucilaginous substances. At the time of use, the powder is diluted with a suitable liquid so as to form a mixture having a consistency appropriate for application to the head.

The powders used in the cataplasms according to this variant of the invention may consist of insoluble substances such as silicas, plants, clays, plants powdered after extraction of their active principle by a solvent or else plants or animals containing non-oxidizing aromatic carbonyl derivatives as defined above.

The diluting liquid may consist of water or of mixtures of water/cosmetically acceptable solvent(s), such as alcohols or glycols, or, alternatively, oils.

The liquid medium is added to the powder in proportions such that, after mixing, a paste is obtained which has a viscosity of between 0.3 and 5 Pa.s.

The dyeing agent for keratinous fibers which is used for carrying out the method according to the invention is essentially characterized in that it comprises at least two separate components (A) and (B) having the composition indicated for the compositions (A) and (B) defined above.

The different compositions (A) and (B) may be packaged in a multi-compartment device also termed "dyeing kit" or "dyeing set" or "dyeing agent" containing all of the components intended to be applied for a given dyeing to the keratinous fibers, in particular the hair, in successive applications with or without premixing.

Devices of this type, according to the invention, may comprise a first compartment containing the composition (A) comprising the monohydroxyindole or dihydroxyindole of formula (I) and a second compartment containing the composition (B) comprising the non-oxidizing aromatic carbonyl derivative or derivatives of formulae (II), (III), (IV) or (V).

Another variant may consist in storing the composition (A) and/or the composition (B) in an anhydrous solvent medium and in then providing a third compartment containing an aqueous medium which is appropriate for dyeing and cosmetically acceptable; in this case, the contents of the third compartment are mixed, just before use, with the contents of one and/or other of the other two compartments containing the anhydrous compositions (A) and/or (B).

The method according to the invention may be carried out by mixing the compositions (A) and (B) just before use, the resulting mixture being applied to the hair for 2 to 60 minutes; this application is followed by rinsing and optionally washing of the hair.

The method according to the invention is preferably carried out by applying the composition (A) in a first stage and the composition (B) in a second stage, rinsing optionally being carried out between the two stages.

It may be used in particular for dyeing human hair which is partially or completely grey or white and may or may not have been permanent-waved, or straightened, or severely or slightly bleached hair, which may have been permanent-waved.

The composition (A) is applied at a temperature compatible with application to the head, that is to say of between 25° and 40° C., for 2 to 60 minutes and preferably 5 to 30 minutes and, after or without intermediate rinsing, the application of the composition (A) is followed by the application of the composition (B) which contains the non-oxidizing aromatic carbonyl derivative. The composition (B) is kept in contact with the hair for 5 to 60 minutes and preferably 10 to 40 minutes, the dyeing temperature also being between 25° and 40° C.

The following examples are intended to illustrate the invention without, however, having a limiting character.

EXAMPLES 1 TO 8

| EXAMPLES 1 TO 8 | | | |
| --- | --- | --- | --- |
| 1 | 2 | 3 | 4 |

| Composition (A) in g of AS | | | | |
|---|---|---|---|---|
| 5,6-Dihydroxyindole | 0.2 | 0.5 | 0.5 | 0.5 |
| Ethyl alcohol | 10 | 10 | 10 | 10 |
| Alkylpolyglycoside sold under the name ORAMIX CG 110 with an AS concentration of 60% by AQUALON | 2.1 | 2.1 | 2.1 | 2.1 |
| Hydroxyethylcellulose sold under the name NATROSOL 250 HHR by AQUALON | 1 | 1 | 1 | 1 |
| Tartric acid | 0.3 | 0.3 | 0.3 | 0.3 |
| Preservative | qs | qs | qs | qs |
| Triethanolamine | 3.75 | 3.75 | 3.75 | 3.75 |
| Water qs | 100 | 100 | 100 | 100 |
| Exposure time (in min) | 15 | 10 | 5 | 20 |
| Intermediate rinsing | yes | yes | no | yes |

EXAMPLES 1 TO 8 (continuation)

| | 5 | 6 | 7 | 8 |
|---|---|---|---|---|
| Composition (A) in g of AS | | | | |
| 5,6-Dihydroxyindole | 0.5 | 0.5 | 0.5 | |
| 2-Carboxy-5,6-dihydroxyindole | | | 0.05 | |
| 2-Methyl-5,6-dihydroxyindole.HBr | | | | 1 |
| Ethyl alcohol | 10 | 10 | 10 | 10 |
| Alkylpolyglycoside sold under the name ORAMIX CG 110 with an AS concentration of 60% by AQUALON | 2.1 | 2.1 | 2.1 | 2.1 |
| Hydroxyethylcellulose sold under the name NATROSOL 250 HHR by AQUALON | 1 | 1 | 1 | 1 |
| Tartric acid | 0.3 | 0.3 | 0.3 | 0.3 |
| Preservative | qs | qs | qs | qs |
| Triethanolamine | 3.75 | 3.75 | 3.75 | 3.75 |
| Water qs | 100 | 100 | 100 | 100 |
| Exposure time (in min) | 20 | 10 | 10 | 15 |
| Intermediate rinsing | yes | no | yes | yes |

10 g of composition (A) are applied to 3 g of hair for the time indicated above, with or without subsequent rinsing.

8 g of composition (B) of Examples 1 to 5 or 5 g of composition (B) of Examples 6 to 8 are then applied for the time indicated in the tables below, the compositions (B) of Examples 1 to 5 being diluted before use with 1.5 times their weight of water and those of Examples 6 to 8 being diluted with 3 times their weight of water.

The hair is then rinsed, washed and then dried.

A uniform dyeing, the shade of which is indicated in the tables below, is finally obtained over the entire head of hair.

TABLE

| | 1 | 2 | 3 | 4 |
|---|---|---|---|---|
| Composition (B) in g of AS | | | | |
| 2-Hydroxy-1,4-napthoquinone | 1 | 1 | | |
| 2-hydroxy-3-methoxy-1,4-napthoquinone | | | | 2.5 |
| 2-Hydroxy-3-methyl-1,4-napthoquinone | 0.15 | 0.15 | 0.5 | |
| 2,5-Dihydroxy-3-methoxy-6-methyl-1,4-benzoquinone | | | 0.3 | |
| Isatin | | | 1.3 | 0.3 |
| Cetyl alcohol | 0.3 | 0.3 | 0.3 | 0.3 |
| Citric acid | 1 | 1 | 1 | 1 |
| Dimethyldistearyl-ammonium chloride | 1 | 1 | 1 | 1 |
| Hydroxypropyl-cellulose | 2.2 | 2.2 | 2.2 | 1.5 |
| Ethyl alcohol | 28.5 | 28.5 | 28.5 | 28.5 |
| Oxyethylenated β-naphthol containing 7 moles of ethylene oxide | 15 | 15 | 15 | 15 |
| Oxyethylenated nonyl-phenol containing 9 moles of ethylene oxide qs | 100 | 100 | 100 | 100 |
| Exposure time (in min) | 10 | 10 | 15 | 10 |
| Shades obtained | | | | |
| on grey hair which is 90% white (Ex. 1-3) on chestnut hair which is 30% white (Ex. 4) | golden coppery blond | golden coppery beige blond | slightly ashy iridescent beige blond | slightly deeper chestnut with auburn glints |

TABLE (continuation)

| | 5 | 6 | 7 | 8 |
|---|---|---|---|---|
| Composition (B) in g of AS | | | | |
| 2-Hydroxy-1,4-naphthoquinone | | | 0.5 | |
| 1,2,4-Trihydroxy-9,10-anthraquinone | | | 4 | |
| 2-Hydroxy-3-methyl-1,4-naphthoquinone | 0.4 | | | |
| 2',5'-Dihydroxy-acetophenone | | | | 2 |
| Isatin | 2 | | | |
| Carob gum sold under the name VIDOGUM L 175 by SANOFI Bio Industrie | | 3 | 3 | 3 |
| Citric acid | 1 | 4 | 4 | 4 |
| Powder of Saponaria spent dues having a particle size of less than 90 micrometers | | 35 | 35 | 35 |
| Powdered skimmed milk qs | | 100 | 100 | 100 |
| Cetyl alcohol | 0.3 | | | |
| Dimethyldistearyl-ammonium chloride | 1 | | | |
| Hydroxypropyl-cellulose | 1.5 | | | |
| Ethyl alcohol | 28.5 | | | |
| Oxyethylenated β-naphthol containing 7 moles of ethylene oxide | 15 | | | |
| Oxyethylenated nonyl-phenol containing 9 moles of ethylene oxide qs | 100 | | | |
| Exposure time (in min) | 10 | 30 | 30 | 30 |
| Shades obtained | | | | |
| on grey hair which is 90% white (Ex. 6-8) on blond hair which is 30% white (Ex. 5) | slightly deeper blond with golden glints | iridescent ash blond | iridescent ash blond | matt natural ash blond |

EXAMPLE 9

COMPOSITION (A):

| | |
|---|---|
| 5,6-Dihydroxyindole | 0.5 g |
| Ethyl alcohol | 10.0 g |
| Hydroxypropylcellulose | 1.0 g |
| Glucoside alkyl ether of formula: | 2.1 g AS |

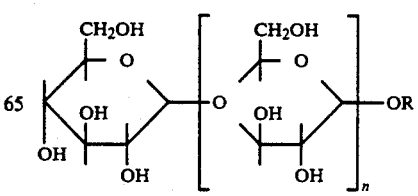

-continued

| | |
|---|---|
| (n = 1 to 5, R denotes $C_8$-$C_{10}$) alkyl sold as formulation containing 60% of active substance (AS) under the name TRITON CG 110 BY ROHM & HAAS | |
| Triethanolamine | 3.75 g |
| Tartric acid | 0.3 g |
| pH = 8.5 | |
| Preservative qs | |
| Water qs | 100.0 g |
| COMPOSITION (B): | |
| 2-Hydroxy-1,4-naphthoquinone | 0.5 g |
| Powder of Saponaria spent residues having a particle size of less than 90 micrometers | 35.0 g |
| Carob gum sold under the name VIDOGUM L 175 by SANOFI BIO INDUSTRIE | 3.0 g |
| Citric acid | 4.0 g |
| Powdered skimmed milk qs | 100.0 g |

The composition (B) is diluted with three times its weight of water and then applied to hair which is 90% white, in an amount of 15 g per 3 g of hair. After an exposure time of 30 minutes, the hair is rinsed and 15 g of composition (A) are then applied. This is left on the hair for 10 minutes.

After rinsing, washing and then rinsing, the hair is dyed a light golden ash blond.

EXAMPLES 10 TO 13

10 g of composition (A) are applied to 3 g of hair for the time indicated in the table below, followed by rinsing.

TABLE

| | 10 | 11 | 12 | 13 |
|---|---|---|---|---|
| Composition (A) in g of AS | | | | |
| 1-Methyl-5,6-dihyroxyindole | 1.5 | | | |
| 2,3-Dimethyl-5,6-dihydroxyindole.HBr | | 0.8 | | |
| 5-Methoxy-6-dihydroxyindole | | | | 1 |
| 3-Methyl-5,6-dihydroxyindole | | | 0.2 | |
| Ethyl alcohol | 10 | 10 | 10 | 10 |
| Alkylpolyglycoside sold under the name ORAMIX CG 110 containing 60% of AS by AQUALON | 2.1 | 2.1 | 2.1 | 2.1 |
| Hydroxyethylcellulose sold under the name NATROSOL 250 HHR by AQUALON | 1 | 1 | 1 | 1 |
| Tartric acid | 0.3 | 0.3 | 0.3 | 0.3 |
| Preservative | qs | qs | qs | qs |
| Triethanolamine | 3.75 | 3.75 | 3.75 | 3.75 |
| Water qs | 100 | 100 | 100 | 100 |
| Exposure time (in min) | 15 | 15 | 15 | 15 |
| Intermediate rinsing | yes | yes | yes | yes |

8 g of composition (B) form Example 10 or 5 g of composition (B) from Examples 11 to 13 are then applied for the time indicated in the table below, the composition (B) of Example 10 being diluted before use with 1.5 times its weight of water and those of Examples 11 to 13 being diluted with 3 times their weight of water.

The hair is then rinsed and then dried.

A uniform dyeing, the shade of which is indicated in the table below, is finally obtained over the entire head of hair.

TABLE

| | 10 | 11 | 12 | 13 |
|---|---|---|---|---|
| Composition (B) in g of AS | | | | |
| 5,8-Dihydroxy-1,4-naphthoquinone | 0.5 | | | |
| 2,2'-Dihydroxybenzophenone | | 0.5 | | |

TABLE-continued

| | 10 | 11 | 12 | 13 |
|---|---|---|---|---|
| 1,2,5,8-Tetrahydroxyanthraquinone | | 3.5 | | 3.5 |
| Carob gum sold under the name VIDOGUM L 175 by SANOFI BIO INDUSTRIE | | | 3 | |
| Sodium carbonate | | 3 | | 3 |
| Powder of Saponaria spent residues having a particle size of less than 90 micrometers | | 35 | 35 | 35 |
| Powdered skimmed milk qs | | 100 | 100 | 100 |
| Cetyl alcohol | 0.3 | | | |
| Citric acid | 1 | | | |
| Dimethyldistearylammonium chloride | 1 | | | |
| Hydroxypropylcellulose | 2.2 | | | |
| Ethyl alcohol | 28.5 | | | |
| Oxyethylenated β-naphthol containing 7 moles of ethylene oxide | 15 | | | |
| Perfume, preservatives | qs | qs | qs | qs |
| Oxyethylenated nonylphenol containing 9 moles of ethylene oxide qs | 100 | | | |
| Exposure time (in min) | 30 | 30 | 30 | 30 |
| Shades obtained | | | | |
| on naturally grey hair which is 90% white | light iridescent beige blond | deep mat ash blond | med. matt ash | |
| on naturally grey hair which is 90% white and has been permanent-waved | | | | slightly iridescent ash |

I claim:

1. A method for dyeing keratinous fibers comprises applying to said fibers a composition (A) comprising in a medium suitable for dyeing said fibers at least one monohydroxyindole or dihydroxyindole present in an amount ranging from 0.05 to 5 percent by weight based on the total weight of said composition (A), the application of said composition (A) to said fibers being preceded or followed by applying to said fibers a composition (B) comprising in a medium suitable for dyeing said fibers at least one non-oxidizing aromatic carbonyl derivative selected from the group consisting of a hydroxyacetophenone, a hydroxybenzophenone, a 2-hydroxy-1,4-benzoquinone, a hydroxy-1,4-naphthoquinone, an amino-1,4-naphthoquinone, a hydroxy-9,10-anthraquinone and an amino-9,10-anthraquinone, said aromatic carbonyl derivative being present in an amount ranging from 0.01 to 5 percent by weight based on the total weight of said composition (B).

2. The method of claim 1 wherein said monohydroxyindole or dihydroxyindole has the formula

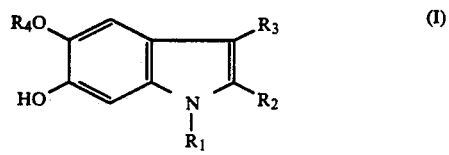

(I)

wherein $R_1$, $R_3$ and $R_4$, each independently, represent hydrogen or $C_1$–$C_4$ alkyl, $R_2$ represents hydrogen, $C_1$–$C_4$ alkyl or carboxyl;

and the corresponding alkali metal, alkaline earth metal, ammonium and amine salts of said compound of formula I, the redox potential of said compound of formula I, measured at pH 7 on a vitreous carbon electrode by voltammetry being less than 200 mV.

3. The method of claim 1 wherein said monohydroxyindole or dihydroxyindole is selected from the group consisting of 5,6-dihydroxyindole,
2-methyl-5,6-dihydroxyindole,
3-methyl-5,6-dihydroxyindole,
1-methyl-5,6-dihydroxyindole,
2,3-dimethyl-5,6-dihydroxyindole,
5-methoxy-6-hydroxyindole and
2-carboxy-5,6-dihydroxyindole.

4. The method of claim 1 wherein said hydroxyacetophenone or said hydroxybenzophenone has the formula

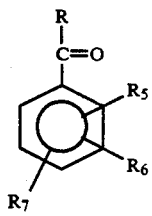

wherein $R_5$, $R_6$ and $R_7$, each independently, represent hydrogen, hydroxyl or methoxy with at least one of $R_5$, $R_6$ and $R_7$ representing hydroxyl, and R represents a methyl or $R_8$, wherein $R_8$ has the formula

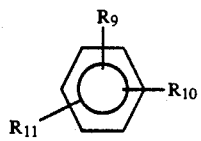

wherein $R_9$, $R_{10}$ and $R_{11}$, each independently, represent hydrogen, hydroxyl or methoxy; said 2-hydroxy-1,4-benzoquinone has the formula

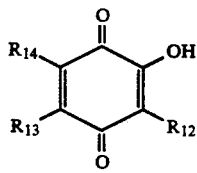

wherein $R_{12}$, $R_{13}$ and $R_{14}$, each independently, represent hydrogen, $C_1$–$C_4$ alkoxy, hydroxyl, $C_1$–$C_4$ alkyl, amino, $C_1$–$C_4$ aminoalkyl or parahydroxyphenyl;

said hydroxy-1,4- naphthoquinone or said amino-1,4-naphthoquinone has the formula

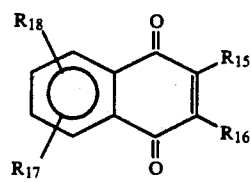

wherein $R_{15}$ and $R_{16}$, each independently, represent hydrogen, chlorine, hydroxyl, methoxy, methyl, isopentyl, acetyl, —$SCH_2COOH$ or —$NR_{19}R_{20}$ wherein $R_{19}$ and $R_{20}$, each independently, represent hydrogen, methyl or hydroxyethyl, and $R_{17}$ and $R_{18}$, each independently, represent hydrogen, hydroxyl, methoxy or methyl, with at least one of $R_{15}$, $R_{16}$, $R_{17}$ and $R_{18}$ representing hydroxyl, or at least one of $R_{15}$ and $R_{16}$ representing —$NR_{19}R_{20}$; and said hydroxy-9,10-anthraquinone or said amino-9,10-anthraquinone has the formula

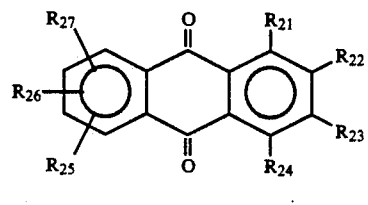

wherein $R_{21}$ to $R_{27}$, each independently, represent hydrogen, chlorine, hydroxyl, methyl, $SO_3M$, $COOM$ or $NR_{28}R_{29}$ wherein M represents hydrogen, Na or K, and $R_{28}$ and $R_{29}$, each independently, represent hydrogen, $C_1$–$C_4$ alkyl or $C_1$–$C_4$ monohydroxylalkyl, at least one of $R_{21}$ to $R_{27}$ representing hydroxyl or $NR_{28}R_{29}$.

5. The method of claim 1 wherein in said composition (B) said aromatic carbonyl derivative is selected from the group consisting of:

2-hydroxyacetophenone,
2,5-dihydroxyacetophenone,
2,6-dihydroxyacetophenone,
4-hydroxy-3-methoxyacetophenone,
3,4,5-trihydroxyacetophenone,
2',2'-dihydroxybenzophenone,
2-hydroxybenzophenone,
2,2',4,4'-tetrahydroxybenzophenone,
3,4,2',4',6'-pentahydroxybenzophenone;
2,5-dihydroxy-1,4-benzoquinone,
2,5-dihydroxy-3-ethyl-1,4-benzoquinone,
2,5-dihydroxy-3,6-dimethoxy-1,4-benzoquinone,
2,5-dihydroxy-3-methyl-6-isopropyl-1,4-benzoquinone,
2,5-dihydroxy-3,6-bis-p-hydroxyphenyl-1,4-benzoquinone,
2-hydroxy-3-methyl-6-methoxy-1,4-benzoquinone,
2-hydroxy-3-methoxy-5,6-methoxy-1,4-benzoquinone,
2-hydroxy-3-methoxy-6-methyl-1,4-benzoquinone,
2,3,5,6-tetrahydroxy-1,4-benzoquinone;
2-hydroxy-3-isopentenyl-1,4-naphthoquinone,
2-hydroxy-3-amino-7-methoxy-1,4-naphthoquinone,
2-hydroxy-3-N-methylamino-1,4-naphthoquinone,
2-hydroxy-6-methoxy-1,4-naphthoquinone,
2-hydroxy-5-methoxy-1,4-naphthoquinone,
2-hydroxy-8-methoxy-1,4-naphthoquinone, 2-hydroxy-5,8-dimethoxy-1,4-naphthoquinone,
2-hydroxy-3-acetyl-1,4-naphthoquinone,
5-hydroxy-2-methoxy-1,4-naphthoquinone,
5-hydroxy-3-dimethylamino-1,4-naphthoquinone,
5-hydroxy-3-methoxy-1,4-naphthoquinone,
5-hydroxy-2-methyl-1,4-naphthoquinone,
5-hydroxy-2-methyl-3-chloro-1,4-naphthoquinone,
5-hydroxy-2-carboxymethylthio-1,4-naphthoquinone,
5-hydroxy-3carboxymethylthio-1,4-naphthoquinone,
5,8-dihydroxy-1,4-naphthoquinone,
5,8-dihydroxy-2-chloro-1,3-naphthoquinone,
2,7-dihydroxy-1,4-naphthoquinone,
5,7-dihydroxy-1,4-naphthoquinone,
3,5-dihydroxy-2methyl-1,4-naphthoquinone,
3,5-dihydroxy-1,4-naphthoquinone,
2,6-dihydroxy-1,4-naphthoquinone,
2,3-dihydroxy-5-methoxy-1,4-naphthoquinone,
2,3-dihydroxy-7-methoxy-1,4-naphthoquinone,
3,6,8-trihydroxy-1,4-naphthoquinone,
2,3,5-trihydroxy-1,4-naphthoquinone,
2,6,7-trihydroxy-1,4-naphthoquinone,
2,3,5,8-tetrahydroxy-1,4-naphthoquinone,
1,4-dihydroxy-9,10-anthraquinone,
1,5-dihydroxy-9,10-anthraquinone,
1,8-dihydroxy-9,10-anthraquinone,
2,6-dihydroxy-9,10-anthraquinone,
1,2,5,8-tetrahydroxy-9,10-anthraquinone,
1,2,3,5,6,7-hexahydroxy-9,10-anthraquinone,
1,8-dihydroxy-3-methyl-9,10-anthraquinone,
1,3,8-trihydroxy-6-methyl-9,10-anthraquinone,
5,8-dichloro-1,4-dihydroxy-9,10-anthraquinone,
the sodium salt of 1,2-dihydroxy-9,10-anthraquinone-3-sulphonic acid,
the sodium salt of 1,2,4-trihydroxy-9,10-anthraquinone-3-sulphonic acid,
1-hydroxyanthraquinone,
2-hydroxyanthraquinone,
1,8-dihydroxy-3-carboxy-9,10-anthraquinone,
1,4,5,8-tetraaminoanthraquinone and
1,4-diaminoanthraquinone.

6. The method of claim 1 wherein said composition (B) contains at least one compound selected from the group consisting of
5,8-dihydroxy-1,4-naphthoquinone,
1,2,5,8-tetrahydroxyanthraquinone and
1,4,5,8-tetraaminoanthraquinone.

7. The method of claim 1 wherein said composition (B) contains at least one compound selected from the group consisting of
2,5-dihydroxy-3-methyl-1,4-benzoquinone,
2,5-dihydroxy-3-methoxy-6-methyl-1,4-benzoquinone,
2-hydroxy-1,4-naphthoquinone,
2-hydroxy-3-methyl-1,4-naphthoquinone,
2,3-dihydroxy-1,4-naphthoquinone,
2,5,7-trihydroxy-1,4-naphthoquinone,
5-hydroxy-1,4-naphthoquinone,
2,5,8-trihydroxy-1,4-naphthoquinone,
2-hydroxy-3-methoxy-1,4-naphthoquinone,
2-carboxy-1-methyl-3,5,6,8-tetrahydroxy-anthraquinone,
1,2-dihydroxyanthraquinone,
1,2,4-trihydroxyanthraquinone,
3-carboxy-1,2,4-trihydroxyanthraquinone, and
2,5-dihydroxy-1,4-naphthoquinone.

8. The method of claim 1 wherein said monohydroxyindole or dihydroxyindole is present in said composition (A) in an amount ranging from 0.05 to 3 percent by weight based on the total weight of said composition (A).

9. The method of claim 1 wherein said aromatic carbonyl derivative is present in said composition (B) in an amount ranging form 0.05 and 3 percent by weight based on the total weight of said composition (B).

10. The method of claim 1 wherein the said medium suitable for dyeing said fibers of said composition (A) and (B) comprises water or a mixture of water and a solvent.

11. The method of claim 1 wherein said medium suitable for dyeing said fibers of said composition (A) or said composition (B) or both is an anhydrous solvent medium.

12. The method of claim 1 wherein the said medium suitable for dyeing said fibers of said composition (B) comprises an anhydrous solvent medium containing at least 15 percent by weight of an anhydrous solvent and at leas 20 percent by weight of at least one anhydrous surfactant.

13. The method of claim 1 wherein said composition (B) is in the form of a powder dilutable at the time of use.

14. The method of claim 1 which includes at the time of use diluting said composition (A) or said composition (B) or both.

15. The method of claim 1 wherein said composition (A) or said composition (B) or both, independently of one another, also contains at least one of anionic, cationic, nonionic or amphoteric surfactant or a mixture thereof; a thickener; a perfume; a sequestering agent; a film-forming agent; a fiber-treatment agent; a dispersing agent; a conditioner; a preservative; an opacifying agent; an agent for swelling keratinous fibers ;a penetrating agent, an antioxidant and a buffer.

16. The method of claim 1 wherein said composition (A) applied to said keratinous fibers is permitted to remain in contact therewith for a period of time ranging from 2 to 60 minutes followed by optionally rinsing said fibers and then applying said composition (B) to said fibers and permitting said composition (B) to remain in contact therewith for a period of time ranging form 5 to 60 minutes.

17. The method of claim 1 wherein said composition (A) applied to said keratinous fibers is permitted to remain in contact therewith for a period of time ranging form 5 to 30 minutes followed by optionally rinsing said fibers and applying said composition (B) to said fibers and permitting said composition to remain in contact therewith for a period of time ranging from 10 to 40 minutes.

18. A dyeing agent for keratinous fibers comprising a composition (A) and a composition (B), each as defined in claim 1 and being successively applicable to said fibers.

19. A multicompartment kit for use in dyeing keratinous fibers comprising a first compartment housing a composition (A) defined in claim 1, a second compartment housing a composition (B) defined in claim 1 and optionally a third compartment housing a medium suitable for dyeing said fibers and for admixing before use with said composition (A) or said composition (B) or both.

* * * * *